United States Patent [19]

Drewlow

[11] Patent Number: Plant 6,631

[45] Date of Patent: Feb. 28, 1989

[54] KALANCHOE PLANT NAMED GARNET

[75] Inventor: Lyndon W. Drewlow, Ashtabula, Ohio

[73] Assignee: Mikkelsens, Inc., Ashtabula, Ohio

[21] Appl. No.: 104,371

[22] Filed: Oct. 5, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinctive Kalanchoe cultivar named Garnet, having deep red flower color, relatively large flower size, deeply lobed leaves, floriferous habit, vigorous growth habit, and excellent keeping qualities.

1 Drawing Sheet

The present invention relates to a new and distinctive cultivar of Kalanchoe plant, botanically known as *Kalanchoe blossfeldiana,* and known by the cultivar name Garnet. Garnet was developed by me through controlled breeding in Ashtabula, Ohio by crossing Mikkelsen Seedling 83-2279-2, the seed parent, with Mikkelsen Seedling 83-2214-2, the pollen parent.

Asexual reproduction by me at Ashtabula, Ohio of stem cuttings of Garnet, of a selection from the progeny of the stated cross, has shown that the unique features of this new Kalanchoe are stabilized and are reproduced true to type in successive propagations.

The following characteristics distinguish the new Kalanchoe from both its parent varieties and other cultivated Kalanchoes of this type known and used in the floriculture industry;

1. Garnet is characterized by its deep red flowers. The flower color is deeper red than Avanti (U.S. Plant Pat. No. 5,962), Pollux (U.S. Plant Pat. No. 4,816) and Attraction (U.S. Plant Pat. No. 5,888) and very similar to Inspiration (U.S. Plant Pat. No. 5,899).

2. Flower size is larger than Inspiration and Avanti, and similar in size to Pollux and Attraction.

3. Flower cluster size and number of flowers for Garnet are greater than Inspiration and Pollux but not as great as Attraction and Avanti.

4. Garnet has better basal branching than Pollux, is similar to Inspiration but not as good as Attraction and Avanti.

5. Garnet is more compact than Inspiration and Pollux but not as compact as Avanti and Attraction.

6. Leaf size is similar to Pollux and Avanti, with Inspiration and Attraction having small leaves.

7. Leaf color is similar to Inspiration, Pollux and Avanti, with Attraction having a lighter green leaf.

8. Garnet has a deeper lobed leaf, with Pollux the next most lobed cultivar, while Attraction, Avanti, and Inspiration have more crenate leaves.

9. Garnet is one week earlier to bloom than Inspiration and Pollux, similar to Avanti, and one week later than Attraction.

10. Garnet has better keeping quality than all of the comparison cultivars mentioned, especially under high light and temperature conditions.

The accompanying colored photograph illustrates in top perspective view the overall appearance of Garnet, with colors being as true as it is reasonably possible to obtain in a colored reproduction of this type.

The following is a detailed description of Garnet based on plants produced under commercial practices in Ashtabula, Ohio under greenhouse conditions during the summer. Color references are made to The Royal Horticultural Society Color Chart, except where general colors of ordinary dictionary significance are used.

Parentage: Controlled cross between female Mikkelsen Seedling 83-2279-2 and male Mikkelsen Seedling 83-2214-2.

Propagation:

(A) *Type cutting.*—2 cm long stem cutting.

(B) *Time to root.*—10 days at 21° C. summer. 14 days at 21° C. winter.

(C) *Rooting habit.*—Abundant; fine, fibrous roots.

Plant description:

(A) *Form.*—Compact, upright growth with good basal branching and a full flower head. Growing and scheduling practices can produce a small plant in a 10 cm pot or a larger plant in a 12 cm pot.

(B) *Habit of growth.*—Vigorous grower with basal branching from almost every node. Basal branches carry large flower clusters whereby upper two-thirds of plant is covered with flowers.

(C) *Foliage.*—Leaves simple, opposite (1) Size: Average full grown leaf of a flowering plant in a 10 cm pot is 100 mm long and 75 mm wide. (2) Shape: Oblong to ovate, apex obtuse, base acute. (3) Texture: Glabrous, succulent, coriaceous. (4) Margin: Pronounced crenate with some lobing. (5) Color: Young foliage, top side 146A, under side 146B. Mature foliage, top side 147A, under side 147B.

Flowering description:

(A) *Flowering habit.*—Inflorescence is a cyme with the terminal flower of the main axis opening first, followed by terminal flowers of the side branches in the inflorescence.

(B) *Natural flowering season.*—Early January. Flowering time under controlled daylength at 20° C. in summer is 11 weeks; in winter is 13 weeks. Flowering time depends on temperature, light intensity and other growing conditions.

(C) *Flower buds.*—Elliptical to oblong, up to 9 mm long, developing to tubular as flower petals mature, sheathed with four green sepals.

(D) *Flowers borne.*—On compound dichasial cymes with primary peduncle 4 mm in diameter, with peduncle length depending on growing conditions and B-9 application. Pedicles are up to 10 mm long.

(E) *Quantity of flowers.*—Very floriferous, with the main axis having over 100 flowers and 6 or more lateral branches having 35 or more flowers.

(F) *Petals.*—(1) Shape: Ovate to almost rounded, top cuspidate. (2) Color: Top side, when opening, 44A, fading to 44B; under side 44C. (3) Number of petals: 4.

(G) *Reproductive organs.*—(1) Stamens: Eight (8) in number. (a) Anther shape: Flat, elliptical, color yellow. (b) Filament color: Light green. (c) Pollen color: Yellow. (2) Pistils (a) Stigma shape:

Flat, color whitish green. (b) Style color: Yellowish green. (c) Ovaries: 4 in number, 4 mm in diameter, green in color.

Disease resistance: No disease problems observed to date.

Other important characteristics: As red flowers age there is almost no fading of color. Other cultivars having red flowers either fade to a lighter color or turn purple as they age, especially under high light.

I claim:

1. A new and distinct cultivar of Kalanchoe plant named Garnet, as described and illustrated.

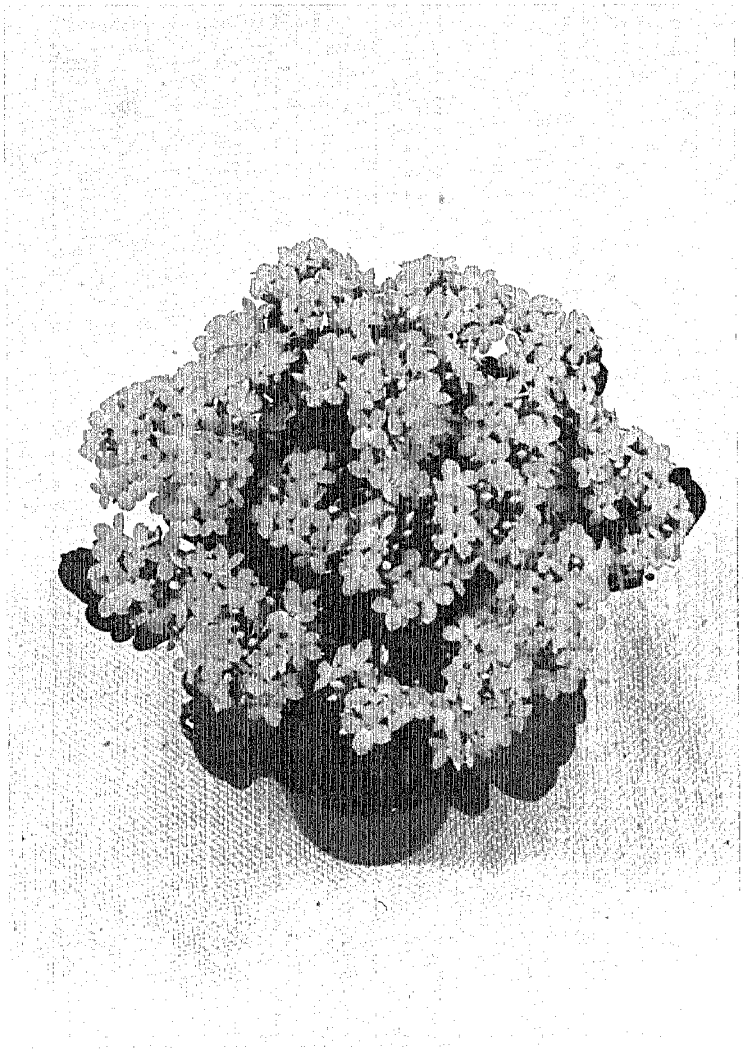

* * * * *